United States Patent [19]

Yang

[11] 4,452,909

[45] Jun. 5, 1984

[54] PROCESS FOR COATING CRYSTALLINE SILICA POLYMORPHS

[75] Inventor: Duck J. Yang, Wallingford, Pa.

[73] Assignee: E. I. Du Pont de Nemours and Company, Wilmington, Del.

[21] Appl. No.: 417,683

[22] Filed: Sep. 13, 1982

[51] Int. Cl.$^3$ .......................... B01J 21/08; B01J 29/06
[52] U.S. Cl. ...................................... 502/69; 502/232
[58] Field of Search .............. 252/455 Z; 502/69, 232

[56] References Cited

U.S. PATENT DOCUMENTS

| | | | |
|---|---|---|---|
| 3,291,754 | 12/1966 | Hanisch et al. | 252/455 Z |
| 3,296,151 | 1/1967 | Heinze et al. | 252/455 Z |
| 3,702,886 | 11/1972 | Arguaer et al. | 423/328 |
| 3,709,979 | 1/1973 | Chu | 423/328 |
| 3,753,929 | 8/1973 | Lindsley | 252/451 |
| 3,832,449 | 8/1974 | Rosinski et al. | 423/328 |
| 3,965,208 | 6/1976 | Butter et al. | 260/671 M |
| 4,061,724 | 12/1977 | Grose et al. | 423/335 |
| 4,073,865 | 2/1978 | Flanigen et al. | 423/339 |
| 4,100,215 | 7/1978 | Chen | 260/671 M |
| 4,104,294 | 8/1978 | Grose et al. | 260/448 C |
| 4,127,616 | 11/1978 | Rodewald | 260/671 R |
| 4,203,869 | 5/1980 | Rollmann | 252/455 Z |
| 4,283,306 | 8/1981 | Herkes | 252/432 |
| 4,330,519 | 5/1982 | Takahashi et al. | 423/335 |

FOREIGN PATENT DOCUMENTS 2079737A 7/1981 United Kingdom .
2084552A 9/1981 United Kingdom .

OTHER PUBLICATIONS

"Silicalite, A New Hydrophobic Crystalline Silica Molecular Sieve", Flanigan et al., Nature, vol. 271, Feb. 9, 1979, pp. 512–516.

*Primary Examiner*—Carl F. Dees

[57] ABSTRACT

Process for coating crystalline silica polymorphs such as silicalites and zeolites with amorphous silica using alkali metal silicates as the source of silica.

7 Claims, No Drawings

PROCESS FOR COATING CRYSTALLINE SILICA POLYMORPHS

BACKGROUND OF THE INVENTION

1. Field Of The Invention

The present invention relates to a process for coating the exterior surfaces of crystalline silica polymorphs, e.g., crystalline silica and aluminosilica type zeolite catalysts with amorphous silica to increase the selectivity of the catalysts.

2. Description Of The Prior Art

The benefits of coating silica containing catalysts such as zeolites, e.g., ZSM 5 and crystalline silicas have been recognized. U.S. Pat. No. 4,203,869 issued on May 20, 1980 discloses a process for coating a zeolite type catalyst to increase the selectivity which process deposits an isocrystalline layer of aluminum-free zeolite over the surface of the zeolite resulting in an aluminum-free outer shell having the same crystal structure as the zeolite. U.S. Pat. No. 4,283,306 issued on Aug. 11, 1981 discloses a group of novel crystalline silicas along with the concept of promoting the catalytic activity of the silicas by the incorporation of certain compounds including amorphous silica. The amorphous silica is placed on the catalyst by the use of certain silicone compounds as described in Column 5, lines 12–38 of the patent. The silicones cannot enter the channels because of their size. However, these compounds are quite expensive relative to the silicates of the present invention. Alumina is coated on the surface of crystalline zeolites by a technique disclosed in U.K. Patent Application No. 2079737 filed on Jul. 6, 1981. U.S. Pat. No. 3,753,929, issued on Aug. 21, 1973, discloses a method for preparing an alumina coated zeolite type catalyst by contacting the zeolite with a soluble aluminum sulfate, or aluminate at a pH 3-5.

Catalysts to which the process of the present invention can be applied are disclosed in U.S. Pat. No. 4,073,865 issued on Feb. 14, 1978, U.S. Pat. No. 4,061,724 issued on Dec. 6, 1977, U.S. Pat. No. 4,330,519 issued on May 18, 1982, U.S. Pat. No. 4,104,294 issued on Aug. 1, 1978, U.K. Patent Application No. 2,084,552 A filed on Sept. 9, 1981 as well as the references disclosed in the foregoing references. The process of the present invention is particularly useful in coating catalysts for the methylation of toluene as disclosed in U.S. Pat. No. 3,965,208 issued on Jun. 22, 1976 and U.S. Pat. No. 4,100,215 issued on Jul. 11, 1978. U.S. Pat. No. 4,127,616 issued on Nov. 28, 1978 which discloses numerous references to disproportionation and alkylation using catalysts which can be coated according to the process of the present invention also discloses coating using bulky silicones.

SUMMARY OF THE INVENTION

This invention is a process for preparing a crystalline silica polymorph having improved selectivity by coating the crystalline silica polymorph with essentially amorphous silica. The coating comprises contacting the silica wherein at least the external portions of channels in the crystal are occupied with a blocking compound with an aqueous solution of an alkali-metal silicate for a period of about 5 minutes to about 1½ hours at a pH in the range 7.5–10.5 to insure the desposition of amorphous silica on the surface of the catalyst but not within the channels. Particularly useful forms of the silica polymorphs to which the process of the present invention is applied are those silica which still contain the template material in their channels.

DETAILED DESCRIPTION OF THE INVENTION

The process of the present invention can be applied to a wide range of crystalline silica polymorphs. The term "crystalline silica polymorph" is used herein to identify the silicas commonly referred to as silicalites and zeolites, especially the aluminosilicate zeolites. Zeolites which benefit from the deposition of an inactive exterior coating provided by the process of the present invention are disclosed for example in U.S. Pat. Nos. 3,702,886, 3,709,979 and 3,832,449. Generally they can also be identified, in terms of mole ratios of oxides and in the anhydrous state, as follows:

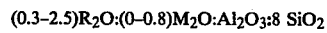

$$(0.3-2.5)R_2O:(0-0.8)M_2O:Al_2O_3:8\ SiO_2$$

wherein R is an organic nitrogen-containing cation derived from two molecules of a hydroxyalkyl trialkylammonium compound and M is an alkali metal cation. The performance of silicalites such as those disclosed in U.S. Pat. Nos. 4,061,724 issued on Dec. 6, 1977, 4,283,306 issued on Aug. 11, 1981, 4,073,865 issued on Feb. 14, 1978, 4,104,294 and the article of Flanigan et al., "Silicalite, A New Hydrophobic Crystalline Silica Molecular Sieve", Nature, Vol. 271, 9 Feb. 1979, pages 512–516 are also improved by the present process.

According to the present invention the intracrystalline channels, i.e., those channels in the crystal, of the silicalite or zeolite are blocked by certain blocking compounds. Since the channels, or at least the outer portions thereof, are blocked, a relatively inexpensive source of silica which would enter unblocked channels can be employed.

The source of silica for the coating process of the present invention is a solution of an alkali metal silicate including silicates selected from the class consisting of sodium silicate, potassium silicate, lithium silicate, rubidium silicate and mixtures comprising the foregoing. Preferably the solution is aqueous. The concentration of this silicate can range from about 1–50% by weight based upon the weight of the solution. Concentrations above 50% are not preferred because the tendency of the silicate to form polymer is increased with increasing concentration. This polymer interfers with the deposition of the silicate and can result in uneven coating. Solutions containing greater than about 50% silicate are quite viscous and for this reason are difficult to handle and to adequately disperse around the material to be coated. The amount of solution which must be contacted with the crystalline silica polymorph in order to obtain a coating of the desired thickness becomes excessive at silicate concentrations below about 1%. It is preferred to employ solutions containing 15–35% by weight of silicate.

The blocking compounds employed in the present invention are contained within the channels of the crystalline silica polymorph. They can be held in the channels mechanically or ionically. These compounds function to prevent the coating composition from filling and irreversibly blocking the channel. The blocking compound can reject the silicate, i.e., prevent any deposit on the blocking compound or can accept the amorphous silica coating which is subsequently removed along with the blocking compound. The blocking compounds need not completely fill the channels of the polymorph but only the exterior portion of a channel and thereby prevent the coating composition from filling the channel. Representative compounds which mechanically block the channels are bulky organic compounds such as triaryl and substituted aryl amines, trialkylamines, triarylalkyl amines and the corresponding phosphines wherein the aryl groups have 6–11 carbon atoms and the alkyl groups have 1–7 carbon atoms. Specific examples of these amines and phosphines include triphenylamine, dimethylphenylamine, tripentamethylphenylamine, triphenylphospine, monoethyldiphenylamine, tri(3-methyl-4-butyl-5-methyl)phenyl amine, trimethylamine, trimethylphenylamine, diphenylmethylamine and the phosphines corresponding to the foregoing. Many compounds which are employed as templates in the formation of the silicas are also operable as blocking compounds. Examples of such compounds are tetraalkyl ammonium ions such as tetra(methyl, ethyl, propyl, butyl)ammonium hydroxide wherein the alkyl group has from 1–7 carbon atoms; aryl and alkyl primary amines wherein the aryl groups have 6–11 carbon atoms and the alkyl groups have 1–12 carbon atoms including n-octyl, cyclohexyl and dodecyl amines; diamines having the formula $NH_2(CH_2)_nNH_2$ wherein n=2–12 such as ethylenediamine and hexamethylenediamine; alcohol amines having the formula $HO(CH_2)_nNH_2$ wherein n is 2–8, e.g, ethanolamine; monohydroxyalkylene trialkyl ammonium halides having the formula HO—R'—N—R$_3$—X wherein R' is an alkylene group having 2–8 carbon atoms, R is an alkyl group having 1–8 carbon atoms and X is a halide selected from the class consisting of chlorine, bromine, iodine and mixtures thereof; alkali and alkali metal alkyl sulfonates such as sodium n-dodecylbenzene sulfonate, n-oxtylbenzene sulfonate, n-heptylbenzene sulfonate, n-hexylbenzene sulfonate, cyclohexylbenzene sulfonate, n-pentylbenzene sulfonate; alkali metal alkyl and aryl acetamides such as sodium oxyethyl actamide, acetamide, aminobenzamide, and phosphines corresponding to the foregoing. Compounds which can be ionically retained in and thereby block the channels are the metallic oxides, and carbonates, e.g., oxides and carbonates of alkali, alkali-earth and transition metals and mixtures thereof, e.g., sodium oxide, iron oxide including the hydrated forms such as ferric oxide hexahydrate, calcium hydroxide, calcium carbonate hexahydrate, magnesium carbonate, magnesium carbonate trihydrate, calcium ferrite, magnesium ferrite and calcium magnesium carbonate.

The blocking compounds should not be soluble in the aqueous silicate system employed as the coating vehicle in the present invention and should be removable only under relatively severe conditions, i.e., the conditions employed to calcine the silica to form an active catalyst and/or the exchange treatment after calcination.

It is necessary to carefully control the pH of the reaction medium to assure the deposition of amorphous silica within a reasonable time. The medium should be maintained in a mildly basic condition i.e., at a pH in the range 7.5–11.5 and preferably in the range 7.5–10.5. The rate of deposition of the amorphous silica decreases with increasing pH to a degree such that no significant deposit of amorphous silica is obtained in 0.5 hour at a pH of 14.0 and a temperature of 80° C.

The present process is conducted at temperatures less than 120° C., usually less than 100° C., and preferably in the range 70°–90° C. This temperature is generally lower than the temperatures employed in the prior art to coat silicas with other materials and insures that amorphous, rather than crystalline, silica is deposited on the base material.

The contact time of the silicate with the base silica can vary from 5 minutes to 1.5 hours depending upon the desired thickness of the coating while depositing essentially amorphous silica on the base material. Usually 5–30 minutes contact time is sufficient to deposit a coating which is thick enough to function effectively. Generally the desired thickness is in the range 20–180Å. If the coating becomes too thick it can bridge over the blocking compounds thereby preventing their removal from the lattice resulting in an inactive catalyst.

Various apparatus for contacting the silicate with the base silica should be apparent to one skilled in the art.

The following Examples are presented to illustrate but not to restrict the present invention. The para-selectivity for xylenes reported herein should be compared to the equilibrium concentration for paraxylene of about 24–25%. Parts and percentages are by weight unless otherwise noted. The $SiO_2$ employed to prepare the crystalline silica polymorph was obtained as a 30% dispersion of colloidal silica in water which contains small amounts of sodium impurity. Such a dispersion is available under the trade name Ludox ® SM.

EXAMPLE 1

A crystalline silica catalyst was prepared by combining 115.2 parts of tetraethyl ammonium bromide in 75 parts of distilled water, 30.6 parts of sodium hydroxide in 33 parts of distilled water and 1270 parts of 30% colloidal silica with vigorous agitation at ambient temperature for approximately 30 minutes and then charging the mixture to an autoclave (Hastelloy C). The autoclave was sealed and the temperature of the contents was raised to 150° C. at the rate of 10° C. per minute with stirring at 75–95 RPM. The contents of the autoclave were stirred for 60 hours at 150° C. following which the resultant slurry was cooled and the solid product recovered by filtration. This solid was then thoroughly washed 3 times each time with a volume of distilled water equal to the volume of the product to remove unreacted salts and other water soluble compounds. The solid was then dried at 95° C. in a nitrogen atmosphere but was not calcined.

Approximately 150 parts of the above prepared solid crystalline silica were added to 600 parts of distilled water. The resultant slurry was heated to 85° C. with stirring and its pH adjusted to approximately 8.5 by the addition of a 5% aqueous solution of sulfuric acid. The slurry was then maintained at 85° C. for approximately 30 minutes following which about 50 parts of a reagent grade, aqueous solution of sodium silicate (30% $SiO_2$-$SiO_2/Na_2O$=3.26 - Density 42.60° Be at 60° F. - Viscosity 775 cP at 68° F. - Diluted with distilled water to a concentration of 20% $SiO_2$) was then added to the slurry over a period of 30 minutes while the pH was maintained at 8.5 by the addition of small amounts of a 5% aqueous solution of sulfuric acid. The slurry was maintained at 85° C. for 1 hour after the addition of sodium silicate then permitted to cool to room temperature following which the slurry was filtered and the solids washed 3 times each time with approximately 4 volumes of distilled water per volume of solid. The foregoing procedure deposited a coating of amorphous silica on the crystalline silica. The coated silica was dried at 95° C. under a nitrogen atmosphere and then calcined by heating it in air at 25°–550° C. with an incremental temperature increase of 1° C./minute, following which the silica was maintained at 550° C. for 4 hours. After calcination the coated silica was exchanged with a 2 N aqueous solution of hydrochloric acid at 95° C. for approximately 16 hours. The silica was filtered, washed and dried at 95° C. in a nitrogen atmosphere. The coated silica was then activated by heating for 4 hours in air at 550° C.

The activated coated silica prepared as above was charged to a quartz tube 1" in diameter and heated to a temperature of approximately 500° C. A mixture of toluene, methanol and hydrogen in a mol ratio of 10/1/8, respectively, was passed over the catalyst at a weight hourly space velocity of 7.7. Approximately 6.4% of the toluene and 94% of the methanol were converted. The percent para-selectivity in xylenes was found to be 89%.

When the above described, activated silica was employed to convert methanol to paraxylene by using the apparatus above-described and passing methanol over the silica at a weight hourly space velocity of 2.0 and at a temperature of 500° C., an 81% para-selectivity in xylenes was obtained.

EXAMPLE 2

The following reactants were combined by vigorous stirring:

| | |
|---|---|
| $(C_3H_7)_4NBr$ | 1000 g |
| NaOH | 175 g |
| $Na_2Al_2O_4.H_2O$ | 60 g |
| $H_2O$ | 3500 g |
| 30% $SiO_2$ | 5000 g |

Approximately one-fifth of the resultant mixture was charged to a one gallon titanium autoclave. The autoclave was sealed and the temperature of the contents was raised to 170° C. with stirring (100 RPM) and maintained at that temperature for approximately 34 hours. The contents of the autoclave were cooled. The solid crystalline aluminosilica product was recovered by filtration, washed three times each time with a volume of the distilled water equal to the volume of the product and then dried at 95° C. under a nitrogen blanket.

Approximately 50 grams of the uncalcined aluminosilica prepared as described above were added to 600 ml of distilled water and the pH of the resulting slurry adjusted to 11 using 50% aqueous caustic. The slurry was then heated to 75° C. and maintained at that temperature for approximately 1 hour following which the pH of the liquid was adjusted to 8.5 with dilute sulfuric acid and 25 ml of sodium silicate solution (as described in Example 1) were then added to the slurry over a period of 30 minutes. The pH of 8.5 and temperature of 75° C. were maintained during the addition and for a period of 1 hour thereafter. The coated aluminosilica was recovered by filtration after cooling the slurry to room temperature. The silica was washed 3 times each time with 3 volumes of distilled water per volume of solid and dried in a nitrogen atmosphere at 95° C., then calcined, exchanged and activated as in Example I.

Approximately 1.8 grams of the above prepared amorphous silica coated aluminosilica was charged to a 1 inch in diameter quartz tube which was externally heated. A mixture of toluene, methanol and hydrogen in a molar ratio of 10/1/8, respectively, was passed over the catalyst at a weight hourly space velocity of 7.7 and a temperature of 450° C. The conversion of toluene was 6.9% and methanol was 87%. The para-selectivity in xylenes was 71%.

EXAMPLE 3

A crystalline metalloaluminosilica (iron, zinc) was prepared by combining the following reactants with vigorous agitation:

| | |
|---|---|
| $(C_2H_5)_4NCl$ | 115.2 g |
| $FeSO_4.7H_2O$ | 1.03 g |
| $Zn(OAc)_2.2H_2O$ | 1.08 g |
| $Na_2Al_2O_4.3H_2O$ | 1.53 g |
| NaOH | 30.6 g |
| $H_2O$ | 175 g |
| 30% $SiO_2$ | 1270 g |

The resultant mixture was then charged to a one gallon autoclave (Hastelloy C). The autoclave was sealed and the temperature of the contents was raised to approximately 150° C. with stirring (100 RPM) and stirred for 60 hours at that temperature. The slurry in the autoclave was then cooled and the solid crystalline product recovered by filtration. After washing the product with water to remove all soluble materials and unreacted compounds, the metalloaluminosilica was dried in a nitrogen atmosphere at 95° C.

Approximately 50 grams of the metalloaluminosilica prepared as described above was added to 500 ml of water and the resultant slurry was adjusted to a pH of 11 with 50% aqueous caustic following which the slurry was heated to 80° C. and held at that temperature for 1 hour. The pH of the slurry was then readjusted to 8.5 using 10% aqueous sulfuric acid and 25 ml of an aqueous sodium silicate solution (as described in Example 1) was added to the slurry over a period of 30 minutes while maintaining a temperature of 80° C. and a pH of 8.5. After maintaining the slurry at 80° C. and a pH of 8.5 for 1 hour after the completion of the addition of the sodium silicate, the slurry was permitted to cool and the amorphous silica coated iron, zinc aluminosilica was recovered by filtration, washed 3 times each time with 3 volumes of water per volume of solid and thereafter dried in a nitrogen blanket at 95° C. This catalyst was then calcined, exchanged and activated according to the procedure described in Example 1.

Approximately 1.8 grams of the amorphous silica coated iron, zinc aluminosilica prepared as described above was charged to a 1 inch diameter quartz tube. A mixture of toluene, methanol and hydrogen in a molar ratio of 10/1/8 was passed over the catalyst at 1 atmosphere pressure and a temperature of 500° C. and at a weight hourly space velocity of 3.9. Approximately 9.6% of the toluene and a 100% of the methanol were converted. A para-selectivity in xylenes of 66% was obtained.

EXAMPLE 4

Approximately 150 grams of natural chabazite having the following composition were added to 600 ml of distilled water.

| Compound | Amount (% by weight) |
|---|---|
| Calcium oxide | 4.8 |
| Iron oxide | 2.1 |

-continued

| Compound | Amount (% by weight) |
| --- | --- |
| Magnesium oxide | 0.8 |
| Potassium oxide | 3.0 |
| Sodium oxide | 0.7 |
| Water | 18.0 |
| Balance — Alumina + Silica | |

The resultant slurry was heated to 80° C. with stirring, adjusted in pH to 11.0 using 50% aqueous sodium hydroxide and maintained at 80° C. for one hour. The pH of the slurry was then adjusted to 8.5 using 20% aqueous sulfuric acid and 100 ml of the above described sodium silicate solution was introduced over a period of 30 minutes. The pH of 8.5 was maintained during the addition of the silicate solution and the temperature of 80° C. was maintained during the addition and for a period of one hour thereafter following which the slurry was cooled to room temperature. The coated chabazite was recovered by filtration, washed three times with distilled water each time with three volumes of water per volume of solid and then dried in a nitrogen blanket at 95° C. The dried, coated chabazite was calcined in air at 25°–550° C. at an incremental increase of 1° C./min. and activated at 550° C. in air for 4 hours.

The calcined product was exchanged two times, each time with 10 grams of a 10% aqueous ammonium nitrate solution for each gram of product the first time at 95° C. for 16 hours and the second time at 95° C. for 4 hours. The exchanged product was recovered by filtration, washed with distilled water to remove all impurities, dried under a nitrogen blanket at 95° C., then activated in air by heating for 4 hours at 550° C.

Approximately 1.5 grams of the exchanged, activated product was charged to a 1" in diameter quartz tubular reactor. The reactor was heated by a split tube furnace to approximately 450° C. and propylene containing 5% helium was directed through the reactor at atmospheric pressure and at a weight hourly space velocity of 4.0. Approximately 3.3% of the propylene was converted to $C_1$–$C_6$ hydrocarbons with about 82% yield to $C_6$ hydrocarbon.

The foregoing demonstrates that the metallic oxides present in the natural chabazite prevented the aqueous silicate solution from plugging the channels and provided a coated catalyst with improved selectivity.

What is claimed is:

1. A process for coating a crystalline silica polymorph with essentially amorphous silica which comprises contacting the silica having the external part of at least a portion of the channels in the crystalline silica polymorph occupied with a blocking compound with an aqueous solution of an alkali metal silicate for a period of about 5 minutes to about 1½ hours while maintaining the pH of the solution in the range 7.5–11.5.

2. The process of claim 1 wherein the crystalline silica is a silicalite.

3. The process of claim 1 wherein the silica is a zeolite.

4. The process of claim 1 wherein the pH is maintained in the range 7.5–10.5.

5. The process of claim 1 wherein the blocking compound is the template employed to prepare the silica polymorph.

6. The process of claims 1, 2, 3, 4 or 5 wherein the temperature of the aqueous solution is maintained in the range 70–90° C.

7. A process for preparing a crystalline silica polymorph coated with amorphous silica which comprises initiating crystallization of silica in a crystallization medium in the presence of a template compound to produce said polymorph, separating the resulting polymorph from the crystallization medium without removing a significant amount of the template compound from the channels in the polymorph, contacting the thus obtained polymorph with an aqueous solution of an alkali metal silicate for a period up to 1½ hours while maintaining the pH of the solution in the range 7.5–10.5 and thereafter separating the unreacted silicate from the polymorph and removing the template compound.

* * * * *